United States Patent
Berge et al.

(10) Patent No.: US 6,506,428 B1
(45) Date of Patent: Jan. 14, 2003

(54) OZONE CLEANING AND SANITATION METHOD AND APPARATUS FOR ICE AND ICE CONVEYANCE SYSTEMS

(75) Inventors: J. Eric Berge, Irvine, CA (US); Mark Allen McClure, Chino Hills, CA (US)

(73) Assignee: Lancer Ice Link, LLC, San Antonio, TX (US)

( * ) Notice: Subject to any disclaimer, the term of this patent is extended or adjusted under 35 U.S.C. 154(b) by 130 days.

(21) Appl. No.: 09/591,804

(22) Filed: Jun. 12, 2000

(51) Int. Cl.[7] ............................. A23L 3/37; F25D 17/02
(52) U.S. Cl. ................ 426/66; 426/67; 62/63; 62/67; 62/344; 422/28
(58) Field of Search ............... 426/66, 67; 62/67, 62/63, 344; 422/28

(56) References Cited

U.S. PATENT DOCUMENTS

| | | |
|---|---|---|
| 3,951,461 A | 4/1976 | De Feudis |
| 4,104,889 A | 8/1978 | Hoenisch |
| 4,124,145 A | 11/1978 | Spinner et al. |
| 4,287,725 A | 9/1981 | Hoenisch |
| 4,827,727 A * | 5/1989 | Caracciolo ............ 62/63 |
| 4,867,052 A | 9/1989 | Cipelletti |
| 4,898,679 A * | 2/1990 | Siegel et al. ............ 210/752 |
| 5,005,364 A * | 4/1991 | Nelson ............ 62/67 |
| 5,458,851 A | 10/1995 | Schroeder et al. |
| 5,482,726 A | 1/1996 | Robinson et al. |
| 5,660,506 A | 8/1997 | Berge et al. |
| 5,824,243 A | 10/1998 | Contreras |
| 5,945,068 A | 8/1999 | Ferone |
| 6,132,629 A | 10/2000 | Boley |
| 6,167,711 B1 * | 1/2001 | Slattery et al. ............ 62/78 |
| 6,231,769 B1 * | 5/2001 | Pean et al. ............ 210/760 |
| 6,334,328 B1 | 1/2002 | Brill |

FOREIGN PATENT DOCUMENTS

| | | | |
|---|---|---|---|
| JP | 410267476 A | * | 3/1997 |
| JP | 09105570 A | * | 4/1997 |
| JP | 411142029 A | * | 5/1999 |

* cited by examiner

*Primary Examiner*—Nina Bhat
(74) *Attorney, Agent, or Firm*—Brown Martin Haller & McClain LLP

(57) ABSTRACT

Apparatus and method are disclosed for production of ice and maintenance of an ice conveyance free of microbial contamination. Ozone is incorporated into water from which the ice is made, so that significant ozone content is present in the ice. This ice may be recovered for human consumption. The ice manufactured in the ice maker is conveyed through a conveyance system to one or more locations remote from the ice maker, where the ice is to be used. Ozone gas is evolved as the ice melts, sublimes or is abraded. The evolved ozone evolved penetrates into all areas of the system and kills substantially all microbial materials which are within the system. Cleanliness is thereafter maintained since passage of more ice and water though the system causes the evolution of additional ozone, which in turn kills any microbial contamination which may subsequently get into the system.

22 Claims, 1 Drawing Sheet

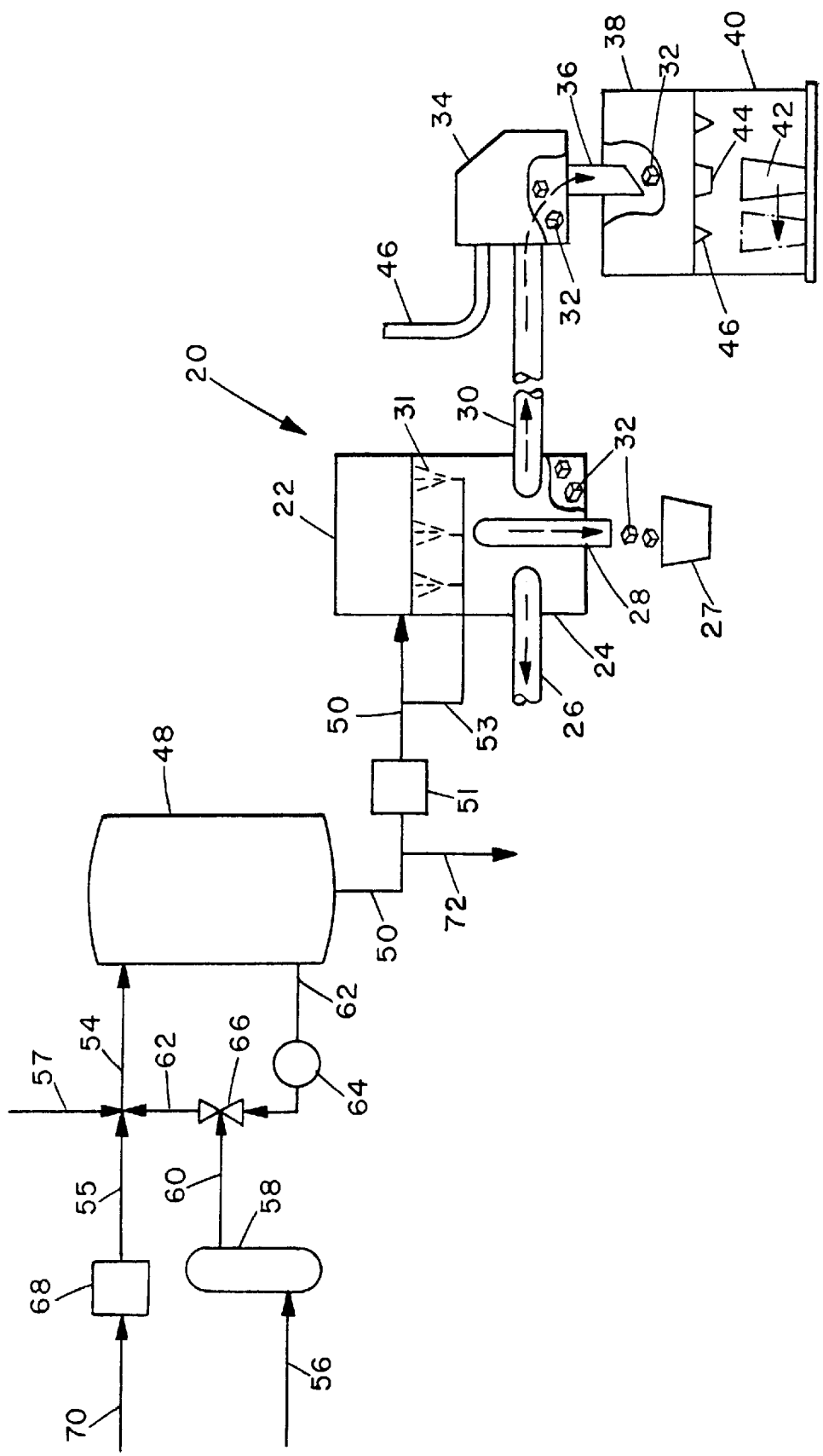

OZONE CLEANING AND SANITATION METHOD AND APPARATUS FOR ICE AND ICE CONVEYANCE SYSTEMS

BACKGROUND OF THE INVENTION

1. Field of the Invention

The invention herein relates to ice manufacturing and conveyance systems. More particularly it pertains to cleaning and sanitation of ice and ice conveyance systems.

2. Description of the Prior Art

Ice conveyance systems are used to move quantities of ice cubes from where they are formed or stored to where they are needed for dispensing for use. A typical application would be in a restaurant (such as a fast food outlet) to move ice cubes from an ice forming machine to an ice and beverage dispenser (IBD) from which the ice cubes can be individually dispensed such as into the beverage containers of the restaurant's patrons.

Water which is used to make ice in such ice conveyance systems will contain varying quantities of foreign materials, notably particulate materials and bacteria. Where water supplies are carefully monitored and treated, as in most municipalities in the major industrial countries, the concentrations of such materials in water supplies are normally maintained at low levels which scientific studies have found to present no significant risks to public health. However, even where the water supplies thus overall contain low, safe levels of particulate materials and bacteria, systems which use such water can contain areas where such particulates and especially bacteria can accumulate to excessive concentrations. As water or ice which is initially free of unsafe concentrations of particulates or bacteria passes into or through such high concentration areas, the water or ice can pick up additional particulates and/or bacteria, sufficient to raise the concentrations of such foreign materials in the water or ice to undesirable levels.

Further, while safe water and ice may be available in larger, more scientifically sophisticated municipalities, in rural areas and in less developed countries water and ice contamination in the form of elevated, undesirable concentrations of particulates, and most especially bacteria, is frequently present. Travellers to many areas are commonly warned to boil or disinfect local water supplies and not to use ice in beverages to avoid becoming ill from such contamination.

Ice conveyance systems can be relatively simple with only one or a few conduits or they can be quite complex with many conduits. In either case the systems almost invariably contain some areas where undesirable levels of contamination, especially bacteria, can accumulate. It is therefore necessary to keep the conduits clean and particularly to keep them free from bacterial contamination. However, cleaning and sanitizing conduits is difficult. It is usually impractical to disassemble the conduits to gain access to their interiors for cleaning, particularly since most conduits are placed in relatively inaccessible locations such as in a suspended ceiling. As a result it has become common in practice to try to clean and sanitize conduits by passing antibacterial and cleansing liquids through the conduits and collecting the spent liquids (with accumulated materials) at one or more outlet points along the conduit runs. This has only been partially successful for several reasons. First, the liquids tend to accumulate at low spots in the conduits, so that stagnant pools of liquid and bacteria remain in the systems. Second, these cleansing liquids are themselves foreign materials in the systems and can leave residues that will contaminate the ice that subsequently passes through the conduits. Third, the cleansing components often are relatively ineffective in removing all bacterial contamination, since bacteria can be lodged in joints and other locations in the conduits which are not accessible to the liquids.

Since most ice conveyance systems are used in food service and beverage service settings, such as restaurants, hotels and motels, hospitals and similar locations, there is of course a great deal of emphasis on keeping the conveyance systems as clean and sanitary as possible. It would therefore be advantageous to have a cleaning and sanitizing system that would be effective throughout an ice conveyance system, would not involve the use of foreign liquids and could be run on essentially a continuous basis.

Ozone ($O_3$) is known to be an oxidizing agent, antiseptic and disinfectant, to be an effective biocidal agent against various pathogens including bacteria and vegetative cells, and to be used for water purification; Brock et al., BIOLOGY OF MICROORGANISMS, pp. 349–351, 544–550 (5th ed., Prentice-Hall: 1988); Sax et al., HAWLEY'S CONDENSED CHEMICAL DICTIONARY, pp. 866–867 (11th ed., Van Nostrand Reinhold: 1987). It has also been reported to have been used to sterilize ice used in cold storage holds of fishing vessels to provide a sterile bed within the holds for the fish catch accumulated while the vessel is at sea.

It would therefore be advantageous if a system were available which could easily and thoroughly clean and sanitize ice during manufacture and conveyance systems for the manufactured ice. It would also be advantageous for that system to be capable of producing clean, uncontaminated ice.

SUMMARY OF THE INVENTION

In the present invention, ozone is injected into the water supply to any ice maker. The presence of the ozone kills bacteria and other microbial contaminants in the water, and ozone content is maintained in the water so that when the water is frozen into ice in an ice maker in the system of the invention, a significant ozone content is present in the ice. This ice may be recovered for human consumption, a definite advantage in those locales where use of ice in beverages and for other food contact must normally be avoided because of microbial contamination.

As a further aspect of the invention, the ice manufactured in the ice maker is conveyed (along with some accompanying water) under gas (usually air) pressure or vacuum through a conveyance system to one or more locations remote from the ice maker, where the ice is to be used. Such conveyance systems are intended for restaurants (especially fast food outlets), hotels, motels, hospitals, and numerous other facilities where ice is required for use by patrons, staff, patients, etc. at locations such as ice and beverage dispensers, ice chests and storage containers, chilled food counters and ice displays, ice bag filling machines, and the like. An unique and particularly preferred system, which conveys ice to remote locations under vacuum, is described and claimed in pending U.S. patent application Ser. No. 09/364,794, filed Jul. 30, 1999, entitled "Vacuum Pneumatic System for Conveyance of Ice."

As the ice and water move through the conduits and components of the conveyance system, ozone is evolved from the water and from the ice as the ice melts, sublimes or is abraded. Similarly, ozone is evolved in the same manner when the ice and water sit in storage containers, either those used for initial distribution of the ice from the ice maker to the conveyance system or those at the remote locations where the ice is to be used. In both cases, the gaseous ozone evolved acts as a powerful oxidizing agent and disinfectant, and kills substantially all microbial materials which are within the system. Since the ozone is a gas, it can penetrate into all areas of the system, including those which liquid cleaners and disinfectants cannot reach, and it can become incorporated into the thin layers of moisture which are present on the interior walls of conduits, diverters, valves, etc., throughout the system, such that it provides superior and thorough cleaning and sanitizing of the system. It is also effective in cleaning and sanitizing the ancillary parts of the system—the ice maker, the receiver bins in remote ice dispensers, storage bins from which ice is drawn at times of high demand, and so forth. Once the microbial contaminants initially present are eliminated, operation of the invention serves to maintain that state of cleanliness, since passage of more ice or water though the system causes the evolution of additional ozone, which in turn kills any microbial contamination which may subsequently get into the system.

In addition, the system operator can also conduct periodic washes of parts or all of the system by running ozonated water from the water supply tank through the system without having to operate the system to make ice. Such water washes are conveniently done at the time of a startup and at intervals (perhaps monthly or quarterly) over the course of regular ice service. Such washes perform a comprehensive cleaning which enhances the ability of the regular operation of the system to maintain a high degree of cleanliness and sanitation in the system and all ancillary equipment.

Numerous microbial contaminants can be controlled or eliminated by this invention, including but not limited to species of Salmonella, Escherichia (including *E. coli*), Campylobacter, Leptospira, Shigella, Enterobacter, Cryptosporidia, Paramecia, and Giardia.

The invention is applicable to conveyance systems of any degree of complexity, with a few or many branches and a few or many remote location ice receivers. It can be used with relatively clean water supplies, such as those from many municipalities, or with water supplies containing significant amounts of particulate matter, such as may be found in rural or underdeveloped areas.

Therefore, in a principal embodiment, the invention involves a method for producing ice which is free of contamination from microbial organisms which comprises providing an ice maker and water for the ice maker; incorporating ozone into the water prior to passage of the water to the ice maker; maintaining the water under conditions to restrict evolution of the ozone from the water prior to freezing of the water in the ice maker, providing ozone-containing water to the ice maker and therein causing the ozone-containing water to freeze to form the ice, such that the ice contains the ozone and is substantially free of any concentration of microbial organisms.

In another principal embodiment, the invention involves a method for controlling the presence of microbial organisms in the interior of an ice conveyance system which comprises: in the ice conveyance system providing an ice maker, an ice receiver, an enclosed conduit through which ice can be conveyed between the ice maker and the ice receiver, and gas flow means for conveying the ice through the conduit; providing water for the ice maker; injecting ozone into the water; thereafter passing the ozone-containing water to the ice maker and causing the ozone-containing water to freeze within the ice maker to form the ice, such that the ice contains the ozone; and thereafter passing the ice containing the ozone from the ice maker through the conduit to the ice receiver; whereby as the ice resides in or passes through the ice maker, conduit and ice receiver, at least some of the ozone is evolved as gas from the ice cubes and disperses throughout interiors of the ice maker, conduit and ice receiver, therein contacting and killing microbial organisms which are present therein.

In yet another principal embodiment the invention is of apparatus for producing ice which is free of contamination from microbial organisms which comprises an ice maker; a supply of water for the ice maker; incorporating means for incorporating ozone into the water prior to supply thereof to the ice maker; and control means for maintaining the water under conditions to restrict evolution of the ozone from the water prior to freezing of the water in the ice maker, such that when the ozone-containing water is frozen in the ice maker to form the ice, the ice contains the ozone and is substantially free of any concentration of microbial organisms.

In yet another principal embodiment the invention is of apparatus for controlling the presence of microbial organisms in the interior of an ice conveyance system comprising the ice conveyance system which itself comprises an ice maker, an ice receiver, an enclosed conduit through which ice can be conveyed between -the ice maker and the ice receiver, and gas flow means for conveying the ice through the conduit; a supply of water for the ice maker; incorporation means for incorporating ozone into the water; the ice maker freezing the ozone-containing water to form the ice, such that the ice contains the ozone; and motivating means for passing harvested ice containing the ozone from the ice maker through the conduit to the ice receiver; such that as the ice resides in or passes through the ice maker, conduit and ice receiver, at least some of the ozone is evolved as gas from the ice cubes and disperses throughout interiors of the ice maker, conduit and ice receiver, therein contacting and killing microbial organisms which are present therein.

Other embodiments and variations will be evident from the descriptions below.

BRIEF DESCRIPTION OF THE DRAWINGS

The single FIGURE of the drawings is a schematic diagram of an embodiment of for ozone-based cleaning and sanitizing of ice and an ice conveyance system.

DETAILED DESCRIPTION AND PREFERRED EMBODIMENTS

For brevity herein, the microorganisms on which the present invention acts will frequently be referred to as "bacteria." It will be understood, however, as discussed below, that bacteria are only exemplary of the various types of microbial organisms, including protozoa and vegetative cells, which can be eliminated from ice and ice conveyance systems according to this invention.

The process and apparatus for using ozone as the cleaning medium to clean and sanitize ice and ice conveyance systems is best understood by reference to the schematic diagram of the FIGURE. The FIGURE illustrates a system 20 which contains a water supply at 48, ice formation at 22 and conveyance of ice as at 30. Considering first the ice conveyance portion of the system 20, there is an ice maker 22 in which ice cubes are made and from which they are dispensed to an ice distributor 24. The ice distributor 24 contains a mechanism (not shown) for dispatching ice cubes through one or more conduits such as 26, 28 and 30. For the purposes of this invention only a single conduit system 30 will be discussed. It will be understood, however, that the conduit system 30 is representative of ice conveyance systems of many sizes and degrees of complexity.

Frequently ice is conveyed through conduits such as 30 by being pushed by high pressure air or other gas (such as nitrogen) from the ice distributor 24. Mechanical impellers, such as augers, or gravitational conveyance (by using inclined conduits) are also used. In the preferred embodiment shown in the diagram, however, the ice conveyance system is operated under vacuum (air at less than ambient pressure) so the stream of air in which the ice cubes 32 are entrained is drawn under vacuum through conduit 30 into a separator 34 in which the ice cubes 32 and the air stream are separated. The ice cubes 32 fall through conduit 36 into an ice receiver 38 which is exemplified at 40 as any one of an ice bin in an ice storage container, a chilled food counter or ice display, an ice bagging machine or an ice and beverage dispenser (IBD). When a user of, for instance, an IBD 40 wishes to obtain an iced beverage he or she will place the container 42 under an ice outlet 44 and activate the ice outlet 44 to dispense ice cubes 32 into the container 42. The use can then position container 42 under a beverage outlet 46 and fill the container 42 with the desired beverage. The air stream in turn is drawn from separator 34 through vacuum line 46 toward a motivating vacuum pump (not shown) and then vented or recycled as desired. It will be evident from this brief description that the conduit system 30, which may be quite complex with numerous bends and branches, as well as the separators 34 at the ends of the various branches, is quite difficult to clean and sanitize effectively.

The unique and improved process of this invention provides in part for treatment of the water from which the ice is made in ice maker 22. Water is provided to a water storage and supply tank 48 through water line 54. The water stored in tank 48, after treatment as described below, is then passed through conduit 50 to ice maker 22, in which ice cubes are made in a conventional manner. Normally the water is supplied to tank 48 through conduit 54 through a line 57 from a clean, potable water supply such as a municipal water system (not shown). As noted, even water rated as "clean" contains some small amount of foreign material, including bacteria, which can accumulate within a system to undesirable levels. In many cases, however, the water supply will not meet that standard. The system of this invention provides for pretreatment of the latter water supplies, and also (if desired) pretreatment of the former water supplies, especially to remove particulate matter. During the process, the water, ice and ice conveyance system also become cleansed of undesirable concentrations of bacteria.

Further, it is recognized that bacteria can infiltrate the system from the ambient atmosphere and accumulate at various locations, such as on the underside of the ice maker 22 where it discharges into dispenser 24.

As to the particulate materials, a particle filter 68 can be placed ahead of line 54, so that contaminated water enters the system 20 through line 70 to the filter 68, and as it passes through the filter 68 particulate matter is removed in a conventional manner. The degree of removal will be dependent upon the type of filter selected and the flow rate of the water. Operation of such particulate removal systems for water is well known and widely described in publications, and many satisfactory commercial filtration devices are available. Filtration systems such as 68 may also be capable of removing some bacterial contamination, but for the purposes of this invention that capability is not necessary.

Water which is at least substantially free of particulate matter thus arrives at tank 48 through line 54, either through line 57 directly from a municipal supply or through line 55 after pretreatment in filter 68. A water circulation conduit 62 leads out of tank 48 and joins conduit 54. A circulation pump 64 in conduit 62 causes water from tank 48 to be circulated through conduit 62 and returned to tank 48 through conduit 54, either alone or mixed with inlet water from lines 55 and/or 57.

Conduit 62 contains a venturi 66 which functions as an aspirator. Input air is supplied through conduit 56 to ozone generator 58 which, usually through conventional electrostatic discharge, converts some of the ordinary oxygen ($O_2$) in the air to ozone ($O_3$). The ozone-rich air exiting from ozone generator 58 is drawn through conduit 60 to venturi 66 where through the aspirator action it is incorporated into the circulating water stream in conduit 62. Return of the ozone-rich circulating water to the tank 48 results in the body of supply water in tank 48 becoming enriched in ozone. The concentration of ozone in the water in tank 48 will be dependent on the amount of water circulating through line 62, the amount of ozone injected into that circulating water at venturi 66 and the average residence time of the larger body of water in tank 48. It is anticipated that the concentration of ozone in the water in tank 48 will be about 0.30–0.50 ppm. Tank 48 will be structured and the fill level maintained so as to minimize the evolution of ozone from the water in tank 48 or line 50. This may be accomplished by any one or more of several techniques, such as keeping the tank completely filled with water, chilling the water and/or maintaining elevated air pressure over the water surface within the tank 48. Chilling the tank water in particular has a significant effect on the incorporation of ozone in the water, since ozone solubility in water is strongly inversely related to the temperature of the water. Water from tank 48 can be drawn off through line 72 from line 50 for determination and monitoring of ozone content. In-line monitoring of ozone concentration as at 51 is also contemplated.

During the sequence of water travel from tank 48 to ice maker 22, the manufacture of ice 32 in ice maker 22, and the movement of that ice 32 through the entire ice conveyance system 20, quantities of the initial ozone content of the water in tank 48 will be evolved. As the ozone-rich water is drawn from supply tank 48 in used to fill the ice molds in ice maker 22, some of the dissolved ozone becomes released from the water and permeates the interior of the ice maker 22. Ozone is a powerful oxidizer and bactericide, and being a gas it reaches into all areas of the interior of the ice maker 22 and, as its concentration builds, kills the accumulated bacteria and thus sanitizes the interior of the ice maker 22.

Ice makers normally do not freeze all of the water which is supplied to them, so that some amount of water is commonly discharged from the ice maker 22 when each batch of ice cubes 32 are harvested, usually on a cycle of approximately about every 10–20 minutes for many commercial ice makers. While it is possible to include equipment with the ice maker to provide for at least some separation of the manufactured ice cubes and the excess water before the ice 32 enters any collection bin or ice conveyance system, that is usually not undertaken. Therefore both ice and water are moved together by the air flow through the conduits 30 and other components of the system 20 and collected in the various bins 38 and other ice receptacles. The presence of the entrained water is beneficial, however, since as noted above it contains some ozone. Therefore, as the ozone-containing water is deposited along the interior surfaces of the bins, conduits, etc., it provides local sterilization.

Because of the low temperature in the ice maker 22, most of the ozone remains in the water as the water freezes to form ice cubes 32 in the ice maker 22, so that the ice cubes 32 are harvested from the ice maker 32 with an ozone content of about 0.20–0.35 ppm. After formation, the ice cubes 32 are released from the ice maker 22 and deposited in the ice dispenser 24. During their stay in the ice dispenser 24 the ice cubes 32 usually melt or sublime slightly, thus releasing some of the gaseous ozone trapped in the ice cubes. This released ozone gas disperses throughout the ice dispenser 24 and, as in ice maker 22, as it concentrates it serves to sanitize the interior of the ice dispenser 24 by killing any bacteria lodged in the ice dispenser 24, including that which may have accumulated on the underside of the ice maker 22.

It is also possible to divert a portion of the ozone-rich water through line 53 into the dispenser 24 where it can be sprayed directly on the underside of the ice maker 22, to eliminate concentrations of bacteria in that location, as shown at 31.

Importantly, however, much of the ozone remains in the ice cubes 32 as they are dispersed from the ice dispenser 24 and pass through the conduit systems, exemplified by conduit 30 and separator 34. As the ice cubes 32 pass through the conduit system 30 they continue to melt and sublime. Also, because the air stream travels through the conduits 30 in a spiraling flow pattern, the conveyed ice cubes 32 are scrubbed against the interior walls of the conduits 30 and are abraded. All of these actions serve to release additional trapped ozone from the ice cubes 32 throughout the conduit system 30. As before, the released gaseous ozone permeates into and concentrates in all of the portions of the conduit system 30, including joints and metal folds, killing any bacteria which have become lodged in the conduit system. Because the ozone is a gas it easily reaches into small pockets and recesses where liquids cannot penetrate, and also contracts all surfaces on the interior of the conduit system, including those which are normally missed by flowing liquid cleaners.

Finally, as the ice cubes 32 reach their final destinations such as ice bin 38, they continue to melt and sublime until dispensed through dispenser 44 to a user's container 42. During their residence time in the bin 38 additional ozone gas is evolved and sanitizes the interior of the bin 38.

It is also contemplated that, since the ozone present in the water from which the ice 32 is made result in substantially bacteria-free ice, ice 32 which is safe for use in beverages can be drawn directly from dispenser 24 as through conduit 28 and collected such as in a beverage container 27.

The amount of ozone in the ice or in the system will vary substantially over time, since ozone is unstable and reverts to common diatomic oxygen ($O_2$) with a "half-life" of about thirty minutes. Thus without replenishment of ozone-containing ice and water in the system, after about two-three hours most of the ozone has disappeared from within the ice in the bins and from within the system conduits and other components.

Therefore, unlike the residual materials from cleaning liquids which remain in the conduit system and can contaminate ice cubes, the ozone concentrations in ice cubes 32 which are deposited in a user's container 42 and melt in the user's beverage, pose no health hazard or other problem for the user. The amount of ozone present as a result of the process of this invention in the ice cubes 32 dispensed to an individual user to chill a drink is on the order of no more than 0.01–0.15 ppm, which is well within the standards for ozone in potable water which have been set by the Food and Drug Administration, and at these concentrations ozone is listed by the FDA as "generally regarded as safe." It will be recognized that the process of this invention operates both to clean and sanitize an ice conveyance system on a first-time basis, and also to maintain that level of sanitation and cleanliness on a on-going basis. Initially it will be useful to run ozone-rich water (with or without ice) through the system, to kill any bacteria and bacterial accumulations at the outset of operations. Thereafter, as the system operates, a level of ozone is created within the system which not only kills incoming bacteria but prevents the formation of any new accumulations of bacteria within the system. Most ice conveyance systems do not move ice continuously, but rather make, harvest and convey ice on an as-needed basis. Thus, for instance, a system installed in a fast food restaurant will typically make ice during the night and convey it to the various locations, such as IBDs, where it will be needed for the next day's service to the restaurant's patrons, until ice receivers at those locations are full. Later, during the day as the ice supplies are diminished at those use locations, the system will intermittently (usually in response to "low ice level" signals from sensors at such locations) make and convey additional quantities of ice to replenish the ice supplies at those locations. Because of ozone's short half-life, the quantity of free ozone within the system will diminish significantly when ice (any accompanying water) is not moving through the system, as the ozone reverts to diatomic oxygen and is not immediately replenished by the passage of more ice. However, this creates no problem of recontamination, since bacterial incursion is minimal during these periods, and any bacteria which may appear are killed as soon as the system resumes conveying ice to the end use locations. If, however, a system is shut down for a prolonged period, such as for maintenance, repair or expansion, there may be some new accumulation of bacteria within the system when it is restarted. The process of the present invention, again preferably with the use of an initial ozonated-water-wash, will adequately remove that and will thereafter continue to keep the restarted system clean and free of bacteria. In addition, it will normally be a useful practice to run an ozonated-water wash through the system periodically, as perhaps once a month or once a quarter. Such initial and periodic water washes (which may be conducted without having to run the system simultaneously in its ice-making or conveying mode) serve to insure that the system is thoroughly clean initially and also enhance the ability of the regular operation of the invention to maintain the desired level of cleanliness and sanitation. Such washes may be with the ozone concentration in the wash water being in the range of about 1.0–5.0 ppm.

The bacteria and other vegetative and microbial contaminants which can be effectively eliminated in ice and ice systems by this invention include species which reside in water or moist areas and which are susceptible to the oxidizing effect of ozone. These include, but are not limited to, various species of Salmonella, Escherichia (including *E. coli*), Campylobacter, Leptospira, Shigella, Enterobacter, Cryptosporidia, Paramecia, and Giardia. Such types of microorganisms are well-known and widely described; see, e.g., Brock et al, supra, ch. 19, especially § 19.20.

The ice has been described above in terms of ice cubes 32. It will understood by those skilled in the art that this device may be used with a wide variety of ice products, including those commonly known as "cube ice" (the above mentioned "ice cubes:), "nugget ice," "bridged ice," "granular ice," "chunk ice" and "crushed ice," or any other form or size of vacuum pneumatically conveyable ice pieces, regardless of the name applied.

It will be evident that there are numerous embodiments of the present invention which are not expressly described above, but which are clearly within the scope and spirit of the invention. The above description is therefore to be considered exemplary only, and the actual scope of the invention is to be defined solely by the appended claims.

We claim:

1. A method for controlling the presence of microbial organisms in the interior of an ice conveyance system which comprises:

in said ice conveyance system providing an ice maker, an ice receiver, an enclosed conduit through which ice can be conveyed between said ice maker and said ice receiver, and gas flow means for conveying said ice through said conduit;

providing water for said ice maker;

injecting ozone into said water;

thereafter passing said ozone-containing water to said ice maker and causing said ozone-containing water to freeze within said ice maker to form said ice, such that said ice contains said ozone; and thereafter passing said ice containing said ozone from said ice maker through said conduit to said ice receiver;

whereby as said ice resides in or passes through said ice maker, conduit and ice receiver, at least some of said ozone is evolved as gas from said ice cubes and disperses throughout interiors of said ice maker, conduit and ice receiver, therein contacting and killing microbial organisms which are present therein.

2. A method as in claim 1 wherein said ozone is evolved as said ice melts, sublimes or is abraded.

3. A method as in claim 1 further comprising said ice maker freezing ice in the form of cube ice, nugget ice, bridged ice, granular ice, chunk ice, crushed ice, or pneumatically conveyable ice pieces.

4. A method as in claim 1 further comprising maintaining said water under conditions to restrict evolution of said ozone from said water prior to freezing of said water in said ice maker, providing said water containing ozone to said ice maker and therein causing said water containing ozone to freeze to form said ice, such that said ice contains said ozone and is substantially free of any concentration of microbial organisms.

5. A method as in claim 4 wherein said conditions under which said water is maintained are conditions of temperature, pressure and containment.

6. A method as in claim 1 wherein ozone concentration in said water is in the range of 0.30–0.50 ppm.

7. A method as in claim 1 wherein ozone concentration in said ice harvested from said ice maker is in the range of 0.20–0.35 ppm.

8. A method as in claim 1 wherein said ozone is created in an ozone generator and passed to a water conduit having a venturi therein, and at least a portion of said water is passed through said conduit and said venturi, said ozone being incorporated into said water during passage of said water through said venturi.

9. A method as in claim 1 wherein said microbial organisms comprise species of Salmonella, Escherichia (including $E.\ coli$), Campylobacter, Leptospira, Shigella, Enterobacter, Cryptosporidia, Paramecia, and Giardia.

10. A method as in claim 1 wherein said ice is conveyed through said system pneumatically, mechanically or gravitationally.

11. A method as in claim 10 wherein said ice is conveyed through said system under gas pressure elevated above ambient air pressure.

12. A method as in claim 10 wherein said ice is conveyed through said system under gas pressure reduced below ambient air pressure.

13. A method as in claim 1 further comprising passing ozone-containing water through at least part of said system prior to start of system operation or at periodic intervals without simultaneous ice production or conveyance for initial sterilization or enhancement of ongoing sterilization.

14. Apparatus for controlling the presence of microbial organisms in the interior of an ice conveyance system comprising:

said ice conveyance system which comprises an ice maker, an ice receiver, an enclosed conduit through which ice can be conveyed between said ice maker and said ice receiver, and gas flow means for conveying said ice through said conduit;

a supply of water for said ice maker;

incorporation means for incorporating ozone into said water;

said ice maker freezing said ozone-containing water to form said ice, such that said ice contains said ozone; and motivating means for passing harvested ice containing said ozone from said ice maker through said conduit to said ice receiver;

such that as said ice resides in or passes through said ice maker, conduit and ice receiver, at least some of said ozone is evolved as gas from said ice cubes and disperses throughout interiors of said ice maker, conduit and ice receiver, therein contacting and killing microbial organisms which are present therein.

15. Apparatus as in claim 14 wherein said ice received comprising a device from which ice conveyed thereto can be obtained by a user of said ice.

16. Apparatus as in claim 15 wherein said device comprises an ice and beverage dispenser, ice bagging device, chilled food counter or ice display, or ice storage cabinet.

17. Apparatus as in claim 14 further comprising control means for maintaining said water under conditions to restrict evolution of said ozone from said water prior to freezing of said water in said ice maker, said control means regulating evolution of ozone from said water by controlling the temperature, pressure and containment environment of said water.

18. Apparatus as in claim 14 wherein said incorporation means incorporates said ozone into said water to an ozone concentration in said water in the range of 0.30–0.50 ppm.

19. Apparatus as in claim 18 wherein said ice maker permits sufficient evolution of ozone therein to reduce ozone concentration in said ice harvested from said ice maker to in the range of 0.20–0.35 ppm.

20. Apparatus as in claim 14 further comprising an ozone generator and wherein said incorporation means comprises a venturi through which at least a portion of said water passes and to which ozone formed in said ozone generator is passed for incorporation therein to said water.

21. Apparatus as in claim 14 wherein said motivation means for conveyance of said ice through said system operates pneumatically, mechanically or gravitationally.

22. Apparatus as in claim 21 wherein said motivation means for conveyance of said ice through said system operates pneumatically and comprises gas at pressure reduced below ambient air pressure.

* * * * *